United States Patent
Yu et al.

(10) Patent No.: US 11,376,297 B2
(45) Date of Patent: Jul. 5, 2022

(54) NUTRITION BLEND FOR HEALTH BENEFITS IN ANIMALS

(71) Applicant: Societe des Produits Nestle SA, Vevey (CH)

(72) Inventors: Ping Yu, St. Louis, MO (US);
Yuanlong Pan, Chesterfield, MO (US)

(73) Assignee: SOCIÉTÉ DES PRODUITS NESTLÉ S.A., Vevey (CH)

( * ) Notice: Subject to any disclaimer, the term of this patent is extended or adjusted under 35 U.S.C. 154(b) by 275 days.

(21) Appl. No.: 16/179,302

(22) Filed: Nov. 2, 2018

(65) Prior Publication Data

US 2019/0134131 A1    May 9, 2019

Related U.S. Application Data

(60) Provisional application No. 62/583,830, filed on Nov. 9, 2017.

(51) Int. Cl.

| | | |
|---|---|---|
| *A61K 36/00* | (2006.01) | |
| *A61K 36/52* | (2006.01) | |
| *A23K 50/40* | (2016.01) | |
| *A61K 36/07* | (2006.01) | |
| *A61K 31/353* | (2006.01) | |
| *A61K 36/9066* | (2006.01) | |
| *A61K 31/01* | (2006.01) | |
| *A61K 31/145* | (2006.01) | |
| *A61K 31/201* | (2006.01) | |
| *A61K 31/202* | (2006.01) | |
| *A61P 35/00* | (2006.01) | |
| *A23K 10/30* | (2016.01) | |
| *A23K 20/121* | (2016.01) | |
| *A23K 20/105* | (2016.01) | |
| *A23K 20/158* | (2016.01) | |
| *A61K 9/00* | (2006.01) | |
| *A61K 36/53* | (2006.01) | |

(52) U.S. Cl.
CPC ............. *A61K 36/52* (2013.01); *A23K 10/30* (2016.05); *A23K 20/105* (2016.05); *A23K 20/121* (2016.05); *A23K 20/158* (2016.05); *A23K 50/40* (2016.05); *A61K 9/0053* (2013.01); *A61K 31/01* (2013.01); *A61K 31/145* (2013.01); *A61K 31/201* (2013.01); *A61K 31/202* (2013.01); *A61K 31/353* (2013.01); *A61K 36/00* (2013.01); *A61K 36/07* (2013.01); *A61K 36/53* (2013.01); *A61K 36/9066* (2013.01); *A61P 35/00* (2018.01)

(58) Field of Classification Search
None
See application file for complete search history.

(56) References Cited

FOREIGN PATENT DOCUMENTS

| | | |
|---|---|---|
| CN | 101253990 A | 9/2008 |
| CN | 104686657 A | 6/2015 |
| FR | 2871342 A1 | 12/2005 |
| RU | 2130738 C1 | 5/1999 |
| RU | 2547172 C1 | 4/2015 |
| WO | 2008087607 A2 | 7/2008 |
| WO | 2011003045 A1 | 1/2011 |

OTHER PUBLICATIONS

Meng, "Whole Process Guidance of Pregnancy, Delivery and Childcare", Jun. 30, 2015, p. 156.
Office Action Received for Application No. CN201880072821.2, dated Aug. 4, 2021, 22 Pages(10 Pages of English Translation and 12 Pages of Official Copy).
International Search Report and Written Opinion, PCT/IB2018/058638 dated Jan. 25, 2019.
Nagel, et al., "Dietary walnuts inhibit colorectal cancer growth in mice by suppressing angiogenesis" Nutrition 2012 28(1):67-75 USA.
Hardman et al., "Suppression of implanted MDA-MB 231 human breast cancer growth in nude mice by dietary walnut" Nutr Cancer 2008 60(5):666-74 USA.
Matsui et al., "Effects of maitake (*Grifola frondosa*) D-Fraction on the carcinoma angiogenesis" Cancer Lett. 2001 172(2):193-8 Japan.
Schley et al., "Mechanisms of omega-3 fatty acid-induced growth inhibition in MDA-MB-231 human breast cancer cells" Breast Cancer Res Treat Jul. 2005;92(2):187-95 Canada.
Zhang et al. "Epigallocatechin-3-gallate(EGCG) suppresses melanoma cell growth and metastasis by targeting TRAF6 activity" Oncotarget. 2016 7(48):79557-79571 China.
Huang, et al. "Lycopene inhibits experimental metastasis of human hepatoma SK-Hep-1 cells in athymic nude mice" J Nutr. 2008 138(3):538-43 Taiwan.
Zhou et al. "Combination of low concentration of (-)-epigallocatechin gallate (EGCG) and curcumin strongly suppresses the growth of non-small cell lung cancer in vitro and in vivo through causing cell cycle arrest" Int J Mol Sci. 2013 14(6):12023-36 China.
Zhou et al., "Dietary Natural Products for Prevention and Treatment of Liver Cancer", Nutrients, vol. 8, Issue No. 156, 2016, pp. 1-23.
Dunaev, "Practical Course of General Chemistry", 2005, p. 33.
Muravieva, "Pharmacognosy (with Herb Biochemistry Fundamentals): Manual", Meditsina, 1978, pp. 23 and 61.
Ponomarev, "Extracting Drug Raw Materials", Meditsina, 1976, pp. 115-120.
Mashkovsky, "Drugs", 14th Edition, vol. 1, 2002, pp. 8-9.
Krosnyuk, "Academy", Pharmaceutical Technology: Drug Formulation Technology: Manual for High School Students, 2nd Edition, 2006, p. 6.

(Continued)

*Primary Examiner* — Michael V Meller

(57) ABSTRACT

Methods and compositions for providing a health benefit to an animal using a nutrient blend. In one embodiment, the method can comprise orally administering a composition comprising at least four of the nutrients selected from the group of walnut, maitake mushroom extract, EGCG, turmeric root powder, lycopene, taurine, EPA, and DHA to the animal.

1 Claim, No Drawings

(56) References Cited

OTHER PUBLICATIONS

Alyautdin, "Pharmacology", 2004, p. 77.
Mashkovsky, "Drugs", 2012, p. 12.
Kharkevich, "Pharmacology: Manual", 10th Edition, 2010, p. 73.
Office Action Received for Application No. RU2020118167, dated Feb. 8, 2022, 24 Pages(10 Pages of English Translation and 14 Pages of Official Copy).
Zheng, "The Science of Functional Foods", Jun. 30, 2009, pp. 263-264.
Xu, "Diet and Cancer Prevention", Dec. 31, 2003, p. 28.
Hua, "New Edition, Treatment of Diseases by Eating", Jul. 31, 2017, p. 3.
Merlin, "Live to 100", Sep. 30, 2010, p. 120.
Office Action Received for Chinese Application No. 201880072821.2, dated Feb. 21, 2022, 26 Pages(11 Pages of English Translation and 15 Pages of Official Copy).

NUTRITION BLEND FOR HEALTH BENEFITS IN ANIMALS

CROSS REFERENCE TO RELATED APPLICATIONS

This application claims priority to U.S. Provisional Application No. 62/583,830 filed Nov. 9, 2017, the disclosure of which is incorporated herein by this reference.

BACKGROUND

One billion people lack access to health care systems. Of the 56.4 million deaths worldwide in 2015, more than half (54%) were due to the top 10 causes. Ischaemic heart disease and stroke are the world's biggest killers, accounting for a combined 15 million deaths in 2015. These diseases have remained the leading causes of death globally in the last 15 years. Chronic obstructive pulmonary disease claimed 3.2 million lives in 2015, while lung cancer (along with trachea and bronchus cancers) caused 1.7 million deaths.

Chronic vascular diseases (CVDs) are the number 1 cause of death globally: more people die annually from CVDs than from any other cause. An estimated 17.7 million people died from CVDs in 2015, representing 31% of all global deaths. Of these deaths, an estimated 7.4 million were due to coronary heart disease and 6.7 million were due to stroke.

Most cardiovascular diseases can be prevented by addressing behavioral risk factors such as tobacco use, unhealthy diet and obesity, physical inactivity and harmful use of alcohol using population-wide strategies.

Cancer is the second leading cause of death globally, and was responsible for 8.8 million deaths in 2015. Globally, nearly 1 in 6 deaths is due to cancer. Approximately 70% of deaths from cancer occur in low- and middle-income countries. Around one third of deaths from cancer are due to the 5 leading behavioral and dietary risks: high body mass index, low fruit and vegetable intake, lack of physical activity, tobacco use, and alcohol use.

Further, according to The Veterinary Cancer Society, cancer is the leading cause of death in 47% of dogs, especially dogs over age ten, and 32% of cats. As of January 2015, 39% of dog owners have a dog aged 7 and older, while 43% of cat owners have a cat in the oldest age bracket. These companion animals are under high risk area for cancer.

Additionally, over 7.5 million children under the age of 5 die from malnutrition and mostly preventable diseases, each year.

As such, the use of novel nutrient blends that can address a variety of health conditions in animals, especially those which can improve the quality of life and life span of the animal, continue to be sought.

SUMMARY

The present disclosure relates generally to nutrient blends that provide a health benefit to an animal. More specifically, the present disclosure relates to methods and compositions utilizing at least four of the nutrients selected from the group of walnut, maitake mushroom extract, EGCG, turmeric root powder, lycopene, taurine, EPA, and DHA.

Accordingly, in a general embodiment, a method of providing a health benefit to an animal can comprise orally administering a composition comprising at least four of the nutrients selected from the group consisting of walnut, maitake mushroom extract, EGCG, turmeric root powder, lycopene, taurine, EPA, and DHA to the animal.

Additionally, in another embodiment, a composition can comprise a nutrient blend, the nutrient blend including at least four nutrients selected from the group consisting of walnut in an amount of 60.61% to 83.33% of the nutrient blend, maitake mushroom extract in an amount of 0.0017% to 0.076% of the nutrient blend, EGCG in an amount of 0.167% to 1.52% of the nutrient blend, turmeric root powder in an amount of 16.67% to 24.24% of the nutrient blend, lycopene in an amount of 0.0167% to 0.033% of the nutrient blend, taurine in an amount of 0.833% to 1.52% of the nutrient blend, EPA in an amount of 0.833% to 6.06% of the nutrient blend, and DHA in an amount of 0.833% to 6.06% of the nutrient blend. Such a nutrient blend can provide a health benefit to an animal.

Such health benefits can include treating or preventing cancer, providing an anti-inflammatory effect, providing an analgesic effect, treating or preventing arthritis, pain management, treating or preventing tendonitis, treating or preventing neurodegenerative diseases, treating or preventing inflammatory bowel disease, treating or preventing retinal disease, treating or preventing autoimmune disease, treating or preventing depression, treating or preventing heart disease, treating or preventing renal or kidney disease, treating or preventing dermatitis, treating or preventing allergies, and treating or preventing liver diseases.

Additional features and advantages are described herein and will be apparent from, the following Detailed Description.

DETAILED DESCRIPTION

Definitions

Some definitions are provided hereafter. Nevertheless, definitions may be located in the "Embodiments" section below, and the above header "Definitions" does not mean that such disclosures in the "Embodiments" section are not definitions.

As used in this disclosure and the appended claims, the singular forms "a," "an" and "the" include plural referents unless the context clearly dictates otherwise. Thus, for example, reference to "an ingredient" or "the ingredient" includes two or more ingredients. The term "and/or" used in the context of "X and/or Y" should be interpreted as "X," or "Y," or "X and Y." Where used herein, the term "example," particularly when followed by a listing of terms, is merely exemplary and illustrative, and should not be deemed to be exclusive or comprehensive.

As used herein, "about" is understood to refer to numbers in a range of numerals, for example the range of −10% to +10% of the referenced number, preferably within −5% to +5% of the referenced number, more preferably within −1% to +1% of the referenced number, most preferably within −0.1% to +0.1% of the referenced number. A range that is "between" two values includes those two values. Furthermore, all numerical ranges herein should be understood to include all integers, whole or fractions, within the range. Moreover, these numerical ranges should be construed as providing support for a claim directed to any number or subset of numbers in that range. For example, a disclosure of from 1 to 10 should be construed as supporting a range of from 1 to 8, from 3 to 7, from 1 to 9, from 3.6 to 4.6, from 3.5 to 9.9, and so forth.

All percentages expressed herein are by weight of the total weight of the composition unless expressed otherwise. When reference is made to the pH, values correspond to pH measured at 25° C. with standard equipment.

The terms "food," "food product" and "food composition" mean a product or composition that is intended for ingestion by an animal and provides at least one nutrient to the animal. The term "pet food" means any food composition intended to be consumed by a dog or a cat.

The term "animal" refers to any animal that could benefit from one or more of the methods or compositions of the present invention including human, avian, bovine, canine, equine, feline, hircine, lupine, murine, ovine, and porcine animal.

The term "companion animal" means a dog or a cat. As used herein, the term "dog" and "canine" can be used interchangeably. In one embodiment, the companion animal can be a canine. In another embodiment, the companion animal can be a cat.

"Wet food" means a pet food having a moisture content from about 50% to about 90%, and in one aspect, from about 70% to about 90%. "Dry food" means a pet food having a moisture content less than about 20%, and in one aspect, less than about 15%, and in a specific aspect, less than about 10%. "Semi-moist food" means a pet food having a moisture content from about 20% to about 50%, and in one aspect, from about 25% to about 35%. "Kibbles" means pieces of dry or semi-moist pet food which can have a pellet shape or any other shape. Non-limiting examples of kibbles include particulates; pellets; pieces of pet food, dehydrated meat, meat analog, vegetables, and combinations thereof; and pet snacks, such as meat or vegetable jerky, rawhide, and biscuits.

The compositions disclosed herein may lack any element that is not specifically disclosed herein. Thus, a disclosure of an embodiment using the term "comprising" includes a disclosure of embodiments "consisting essentially of" and "consisting of" the components identified. Similarly, the methods disclosed herein may lack any step that is not specifically disclosed herein. Thus, a disclosure of an embodiment using the term "comprising" includes a disclosure of embodiments "consisting essentially of" and "consisting of" the steps identified. Moreover, the description of some steps as "optional" does not imply that the other steps which are not explicitly described as optional are necessarily required.

Any embodiment disclosed herein can be combined with any other embodiment disclosed herein.

"Prevention" includes reduction of risk and/or severity of a condition or disorder. The terms "treatment," "treat," "treating," and "to alleviate" include both prophylactic or preventive treatment (that prevent and/or slow the development of a targeted pathologic condition or disorder) and curative, therapeutic or disease-modifying treatment, including therapeutic measures that cure, slow down, lessen symptoms of, and/or halt progression of a diagnosed pathologic condition or disorder; and treatment of patients at risk of contracting a disease or suspected to have contracted a disease, as well as patients who are ill or have been diagnosed as suffering from a disease or medical condition. The term does not necessarily imply that a subject is treated until total recovery. The terms "treatment," "treat," and "treating" also refer to the maintenance and/or promotion of health in an individual not suffering from a disease but who may be susceptible to the development of an unhealthy condition. The terms "treatment," "treat," "treating," and "to alleviate" are also intended to include the potentiation or otherwise enhancement of one or more primary prophylactic or therapeutic measure. The terms "treatment," "treat," "treating" and "to alleviate" are further intended to include the dietary management of a disease or condition or the dietary management for prophylaxis or prevention a disease or condition. A treatment can be patient- or doctor-related.

The relative terms "improved," "increased," "enhanced" and the like refer to the effects of the composition disclosed herein (a composition comprising a therapeutically effective amount of any of the nutrients described herein or a prophylactic dose of any of the nutrients described herein) relative to a composition having a lower amount or lacking any of the nutrients described herein, but otherwise identical.

As used herein "walnut" refers to any walnut species, including without limitation English walnut and black walnut, and include any portion or processing thereof including without limitation whole nut, ground walnut, walnut meal, and the like.

As used herein "maitake mushroom extract" refers to the mushroom *Grifola frondosa* and includes any portion thereof or any extract thereof.

Embodiments

An aspect of the present disclosure is a method of providing a health benefit to an animal comprising orally administering a composition comprising at least four of the nutrients selected from the group consisting of walnut, maitake mushroom extract, EGCG, turmeric root powder, lycopene, taurine, EPA, and DHA to the animal.

Additionally, in another embodiment, a composition can comprise a nutrient blend, the nutrient blend including at least four nutrients selected from the group consisting of walnut in an amount of 60.61% to 83.33% of the nutrient blend, maitake mushroom extract in an amount of 0.0017% to 0.076% of the nutrient blend, EGCG in an amount of 0.167% to 1.52% of the nutrient blend, turmeric root powder in an amount of 16.67% to 24.24% of the nutrient blend, lycopene in an amount of 0.0167% to 0.033% of the nutrient blend, taurine in an amount of 0.833% to 1.52% of the nutrient blend, EPA in an amount of 0.833% to 6.06% of the nutrient blend, and DHA in an amount of 0.833% to 6.06% of the nutrient blend. Such a nutrient blend can provide a health benefit to an animal.

Generally, the methods and compositions include various nutrients that provide a health benefit to the animal. Such nutrients can include walnut, maitake mushroom extract, EGCG, turmeric root powder, lycopene, taurine, EPA, and DHA. In various aspects, the composition can comprise at least 4 nutrients, 5 nutrients, 6 nutrients, 7 nutrients, or in one specific aspect, all 8 nutrients. In one aspect, the composition can include at least 4 nutrients including maitake mushroom extract, turmeric root powder, taurine, and walnut.

Generally, the nutrients can be present in a therapeutically effective amount to provide a health benefit to an animal. Such nutrients can be present in various concentrations depending on the composition. In one embodiment, the composition can be a food. In such an embodiment, the nutrients can be present as follows: the walnut can be present in an amount of 5% to 20%, in one aspect, the walnut can be present in an amount of 10% to 15%; the maitake mushroom extract can be present in an amount of 0.0001% to 0.05%, in one aspect, the maitake mushroom extract can be present in an amount of 0.0001% to 0.025%; EGCG can be present in an amount of 0.01% to 0.5%, in one aspect, EGCG can be present in an amount of 0.05% to 0.1%; the turmeric root powder can be present in an amount of 1% to 8%; in one aspect, the turmeric root powder can be present in an amount of 3% to 5%; lycopene can be present in an amount of 0.001% to 0.01%; in one aspect, lycopene can be present in an amount of 0.005% to 0.008%; taurine can be present in an amount of 0.05% to 0.5%, in one aspect, taurine can be present in an amount of 0.1% to 0.3%; EPA can be present in an amount of 0.05% to 2%, in one aspect, EPA can be present in an amount of 0.1% to 1%; and DHA can be present in an amount of 0.05% to 2%, in one aspect, DHA can be present in an amount of 0.1% to 1%.

Additionally, in another embodiment, the composition can be a supplement. In such an embodiment, the nutrients can be present as follows: the walnut is present in an amount of 60.61% to 83.33% of the supplement, the maitake mushroom extract is present in an amount of 0.0017% to 0.076% of the supplement, the EGCG is present in an amount of 0.167% to 1.52% of the supplement of the supplement, the turmeric root powder is present in an amount of 16.67% to 24.24% of the supplement, the lycopene is present in an amount of 0.0167% to 0.033% of the supplement, the taurine is present in an amount of 0.833% to 1.52% of the supplement, the EPA is present in an amount of 0.833% to 6.06% of the supplement, and the DHA is present in an amount of 0.833% to 6.06% of the supplement.

Such combinations of nutrients can provide a health benefit to an animal. In one embodiment, the health benefit can be anyone of the following: treating or preventing cancer, providing an anti-inflammatory effect, providing an analgesic effect, treating or preventing arthritis, pain management, treating or preventing tendonitis, treating or preventing neurodegenerative diseases, treating or preventing inflammatory bowel disease, treating or preventing retinal disease, treating or preventing autoimmune disease, treating or preventing depression, treating or preventing heart disease, treating or preventing renal or kidney disease, treating or preventing dermatitis, treating or preventing allergies, and treating or preventing liver diseases.

The present nutrient blends can be used in conjunction with any diet or regime. As discussed, the nutrient blend can be part of a food or a supplement. In one aspect, the food can be a pet food. In another aspect, the food can be a complete and nutritionally balanced pet food. In another embodiment, the nutrient blend can be part of a treat, gravy, or other companion food item. The present nutrient blends can be used for imparting a health benefit to any animal. In one aspect, the animal can be a companion animal. In another aspect, the companion animal can be a dog. In another aspect, the companion animal can be a cat.

Generally, the present nutrient blends can be administered for sufficient time to impart a health benefit to an animal. In one embodiment, the administration can be on a regular basis. In some embodiments, the nutrient blends can be administered to the companion animal for a time period of at least one week, at least one month, at least two, three, four, five or six months; and in some embodiments, for at least one year, or even for the duration of the animal's life. During the time period, the nutrient blends can be administered to the dog at least one day per week, at least two days per week, at least three, four, five or six days per week; or even seven days per week. The nutrient blends can be administered in a single dose per day or in multiple separate doses per day.

In an embodiment, the nutrient blends can be administered in an amount that provides about 0.1 g to 10 g of walnut per kg body weight of the animal per day. In one aspect, 0.5 g to about 6.5 g of the walnut per kg body weight of the animal can be administered per day. In an embodiment, the nutrient blends can be administered in an amount that provides about 0.1 mg to 30 mg of maitake mushroom extract per kg body weight of the animal per day. In one aspect, 0.15 mg to about 20 mg of the maitake mushroom extract per kg body weight of the animal can be administered per day. In an embodiment, the nutrient blends can be administered in an amount that provides about 0.5 mg to 200 mg of EGCG per kg body weight of the animal per day. In one aspect, 1 mg to about 180 mg of the EGCG per kg body weight of the animal can be administered per day. In an embodiment, the nutrient blends can be administered in an amount that provides about 0.05 g to 5 g of turmeric root powder per kg body weight of the animal per day. In one aspect, 0.1 g to about 4 g of the turmeric root powder per kg body weight of the animal can be administered per day. In an embodiment, the nutrient blends can be administered in an amount that provides about 0.005 g to 1 g of lycopene per kg body weight of the animal per day. In one aspect, 0.01 g to about 0.5 g of the lycopene per kg body weight of the animal can be administered per day. In an embodiment, the nutrient blends can be administered in an amount that provides about 1 mg to 300 mg of taurine per kg body weight of the animal per day. In one aspect, 5 mg to about 200 mg of the taurine per kg body weight of the animal can be administered per day. In an embodiment, the nutrient blends can be administered in an amount that provides about 1 mg to 1000 mg of EPA per kg body weight of the animal per day. In one aspect, 5 mg to about 750 mg of the EPA per kg body weight of the animal can be administered per day. In an embodiment, the nutrient blends can be administered in an amount that provides about 1 mg to 1000 mg of DHA per kg body weight of the animal per day. In one aspect, 5 mg to about 750 mg of the DHA per kg body weight of the animal can be administered per day.

The pet food compositions disclosed herein can be any food formulated for consumption by a pet such as a dog. In an embodiment, the pet food composition provides complete nutrition as defined by the Association of American Feed Control Officials (AAFCO) and which depends on the type of animal for which the composition is intended (e.g., a dog).

The pet food composition can comprise meat, such as emulsified meat. Examples of suitable meat include poultry, beef, pork, lamb and fish, especially those types of meats suitable for pets. The meat can include any additional parts of an animal including offal. Some or all of the meat can be provided as one or more meat meals, namely meat that has been dried and ground to form substantially uniform-sized particles and as defined by AAFCO. Additionally or alternatively, vegetable protein can be used, such as pea protein, corn protein (e.g., ground corn or corn gluten), wheat protein (e.g., ground wheat or wheat gluten), soy protein (e.g., soybean meal, soy concentrate, or soy isolate), rice protein (e.g., ground rice or rice gluten) and the like.

The pet food compositions disclosed herein can comprise one or more of a vegetable oil, a flavorant, a colorant or water. Non-limiting examples of suitable vegetable oils include soybean oil, corn oil, cottonseed oil, sunflower oil, canola oil, peanut oil, safflower oil and the like. In some embodiments, the lipids in the composition can include MCTs or one or more of any vegetable oil, any fish oil, the lipid from any meat, and any omega-3 fatty acids.

Non-limiting examples of suitable flavorants include yeast, tallow, rendered animal meals (e.g., poultry, beef, lamb, pork), flavor extracts or blends (e.g., grilled beef), animal digests, and the like. Non-limiting examples of suitable colorants include FD&C colors, such as blue no. 1, blue no. 2, green no. 3, red no. 3, red no. 40, yellow no. 5, yellow no. 6, and the like; natural colors, such as caramel coloring, annatto, chlorophyllin, cochineal, betanin, turmeric, saffron, paprika, lycopene, elderberry juice, pandan, butterfly pea and the like; titanium dioxide; and any suitable food colorant known to the skilled artisan.

The pet food compositions disclosed herein can optionally include additional ingredients, such as starches, humectants, oral care ingredients, preservatives, amino acids, fibers, prebiotics, sugars, animal oils, aromas, other oils additionally or alternatively to vegetable oil, salts, vitamins, minerals, probiotic microorganisms, bioactive molecules or combinations thereof.

Non-limiting examples of suitable starches include a grain such as corn, rice, wheat, barley, oats, potatoes, peas, beans, cassava, and the like, and mixtures of these grains, and can be included at least partially in any flour. Non-limiting examples of suitable humectants include salt, sugars, propylene glycol and polyhydric glycols such as glycerin and sorbitol, and the like. Non-limiting examples of suitable oral care ingredients include alfalfa nutrient concentrate containing chlorophyll, sodium bicarbonate, phosphates (e.g., tricalcium phosphate, acid pyrophosphates, tetrasodium pyrophosphate, metaphosphates, and orthophosphates), peppermint, cloves, parsley, ginger and the like. Non-limiting examples of suitable preservatives include potassium sorbate, sorbic acid, sodium methyl para-hydroxybenzoate, calcium propionate, propionic acid, and combinations thereof.

Specific amounts for each additional ingredient in the pet food compositions disclosed herein will depend on a variety of factors such as the ingredient included in the first edible material and any second edible material; the species of animal; the animal's age, body weight, general health, sex, and diet; the animal's consumption rate; the purpose for which the food product is administered to the animal; and the like. Therefore, the components and their amounts may vary widely.

EXAMPLE

By way of example and not limitation, the following non-limiting study is illustrative of compositions and methods using nutrient blends in animals, in one or more embodiments provided by the present disclosure.

Example 1

Nutrient Blend Study

Female nude mice with 3-4 weeks age (n=50) were randomized into 10 groups based on the baseline body weight (n=4 to 5/group) which were assigned to one of the ten diets randomly till end of study with one-week transition from original diet to experimental diets. All the diets were freely accessed to the mice. Every week fresh diet was weighted and provided three times to mice. Six weeks after feeding experimental diets, $1\times10^6$ human breast cancer cell line MDA-MB231 was subcutaneously injected into right flank of each mouse. Tumor occurrence and size was recorded and measured by caliper every two weeks.

The following diets were used in the study. Control: AIN-93G (available from Research diets, Inc.) (18% protein, 7.2% fat, 63% carbohydrate, 5% fiber, remaining % moisture). AIN-93G+nutrient blend (NB) (replacing 16.46% carbohydrate with 11.3% whole walnut meal, 0.005% maitake mushroom extract, 0.05% EGCG, 3% turmeric root powder, 0.005% lycopene, 0.1% taurine, and 2% fish oil) having 19.9% protein, 9.7% fat, 53.2% carbohydrate, 6.1% fiber, and 11.1% moisture. AIN-93G+turmeric root powder (replacing 3% carbohydrate with 3% turmeric root powder) having 18% protein, 7.2% fat, 63% carbohydrate, 5% fiber, and 6.8% moisture. AIN-93G+EGCG (replacing 0.05% carbohydrate with 0.05% EGCG) having 18% protein, 7.2% fat, 63% carbohydrate, 5% fiber, and 6.8% moisture. AIN-93G+EGCG+turmeric root powder (replacing 0.05% carbohydrate with 0.05% EGCG and replacing 3% carbohydrate with 3% turmeric root powder) having 18% protein, 7.2% fat, 63% carbohydrate, 5% fiber, and 6.8% moisture. AIN-93G+lycopene (replacing 0.005% carbohydrate with 0.005% lycopene) having 18% protein, 7.2% fat, 63% carbohydrate, 5% fiber, and 6.8% moisture). AIN-93G+fish oil (available from Omega Protein) (replacing 2% carbohydrate with 2% fish oil) having 18% protein, 7.2% fat, 63% carbohydrate, 5% fiber, and 6.8% moisture. AIN-93G+taurine (replacing 0.1% carbohydrate with 0.1% taurine) having 18% protein, 7.2% fat, 63% carbohydrate, 5% fiber, and 6.8% moisture. AIN-93G+maitake mushroom extract (available from Aloha Medicinals Inc.) (replacing 0.0005% carbohydrate with 0.0005% maitake mushroom extract) having 18% protein, 7.2% fat, 63% carbohydrate, 5% fiber, and 6.8% moisture. AIN-93G+walnut meal (Oh! Nuts® available from www.ohnuts.com) (replacing 11.3% carbohydrate with 11.3% walnut) having 21% protein, 8% fat, 57.5% carbohydrate, 5% fiber, and 8.5% moisture. Nutrient blend (NB) composition: 11.3% whole walnut meal, 0.005% maitake mushroom extract, 0.05% EGCG, 3% turmeric root powder, 0.005% lycopene, 0.1% taurine, and 2% fish oil.

The results of the study show that only the "NB" composition reduced cancer occurrence (Table 1), and slowed down cancer growth (Table 2 and 3). Single nutrient supplemented compositions failed to reach similar preventive effects. The data clearly demonstrate that the NB composition provided unexpected cancer prevention effects, which cannot be achieved by single nutrient compositions. Further, the combination of EGCG and "turmeric root powder" also failed to show any cancer prevention effects, which disproves the published cancer treatment effects of EGCG and "Turmeric root powder" as reported in Zhou D H, Wang X, Yang M, Shi X, Huang W, Feng Q. "Combination of low concentration of (−)-epigallocatechin gallate (EGCG) and curcumin strongly suppresses the growth of non-small cell lung cancer in vitro and in vivo through causing cell cycle arrest" Int J Mol Sci. 2013; 14(6):12023-36. The present results are wholly unexpected as the present NB blend utilized EGCG, fish oil, and maitake mushroom extract which individually increased tumor sizes vs the control diet (see Table 2). The present NB composition delivered a strong cancer treatment in animals and can be used for prevention or treatment for animals that are high risk of cancer as well as in animals having completed cancer treatments.

TABLE 1

| Group | Tumor Occurrence (2 weeks after tumor inoculation) | Tumor Growth (6 weeks after tumor inoculation) |
| --- | --- | --- |
| Control diet | 5/5 | 5/5 |
| Turmeric root powder diet | 5/5 | 5/5 |
| EGCG diet | 5/5 | 5/5 |
| EGCG + Turmeric root powder diet | 5/5 | 5/5 |
| Lycopene diet | 5/5 | 5/5 |
| Fish oil diet | 5/5 | 5/5 |
| Taurine diet | 4/4 | 4/4 |
| Mushroom diet | 5/5 | 5/5 |
| Walnut diet | 5/5 | 4/5 |
| NB diet | 5/5 | 3/5 |

TABLE 2

| Group | Mean Tumor Size (mm$^3$) |
| --- | --- |
| Control diet | 190.09 |
| Turmeric root powder diet | 57.73 |
| EGCG diet | 186.31 |
| EGCG + Turmeric root powder | 130.39 |
| Lycopene diet | 124.54 |
| Fish oil diet | 274.14 |
| Taurine diet | 78.27 |
| Mushroom diet | 256.57 |
| Walnut diet | 175.92 |
| NB diet | 19.40 |

TABLE 3

| Group | Tumor-free (0) | Reversible stage (<10 mm³) | Stage I (<25 mm³) | Stage II (<50 mm³) | Stage III (<100 mm³) | Stage IV (<200 mm³) | Stage V (<400 mm³) | Stage VI (<800 mm³) |
|---|---|---|---|---|---|---|---|---|
| Control diet | | | | | 20% | 40% | 40% | |
| Turmeric root powder diet | | | 20% | 20% | 60% | | | |
| EGCG diet | | | | 40% | | 20% | 20% | 20% |
| EGCG + Turmeric root powder diet | | | 40% | 20% | | 20% | | 20% |
| Fish oil diet (source of DHA & EPA) | | | | 20% | | 40% | 20% | 20% |
| Lycopene diet | | | | | 60% | 20% | 20% | |
| Maitake Mushroom diet | | | 20% | 20% | | 20% | 40% | |
| Taurine diet | | | 25% | | 25% | 50% | | |
| Walnut diet | 20% | | | 40% | | | 20% | 20% |
| NB diet | 40% | 40% | | | 20% | | | |

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The invention is claimed as follows:

1. A composition comprising:
   a) walnut in an amount of 60.61% to 83.33% of the total composition;
   b) maitake mushroom extract in an amount of 0.0017% to 0.076% of the total composition;
   c) Epigallocatechin gallate in an amount of 0.167% to 1.52% of the total composition;
   d) turmeric root powder in an amount of 16.67% to 24.24% of the total composition;
   e) lycopene in an amount of 0.0167% to 0.033% of the total composition;
   f) taurine in an amount of 0.833% to 1.52% of the total composition;
   g) eicosapentaenoic acid in an amount of 0.833% to 6.06% of the total composition; and
   h) docosahexaenoic acid in an amount of 0.833% to 6.06% of the total composition.

\* \* \* \* \*